(12) United States Patent
Germaneau et al.

(10) Patent No.: US 8,771,653 B2
(45) Date of Patent: Jul. 8, 2014

(54) ANTI-ULTRAVIOLET ADDITIVE COMPRISING A $UV_A$ FILTER, A $UV_B$ FILTER AND AN OIL THAT IS A SOLVENT FOR SAID FILTERS, AND USE THEREOF IN COLOURED AND/OR PERFUMED COMPOSITIONS

(75) Inventors: Sylvie Germaneau, Saint Jean de Braye (FR); Valérie Alard, Orleans (FR); Eric Perrier, Les Cotes d'Arey (FR); Maud Guyot, Chateauneuf sur Loire (FR)

(73) Assignee: LVMH Recherche, Saint Jean de Braye (FR)

( * ) Notice: Subject to any disclaimer, the term of this patent is extended or adjusted under 35 U.S.C. 154(b) by 0 days.

(21) Appl. No.: 13/554,200

(22) Filed: Jul. 20, 2012

(65) Prior Publication Data

US 2013/0046029 A1    Feb. 21, 2013

(30) Foreign Application Priority Data

Jul. 21, 2011   (FR) ...................................... 11 56646

(51) Int. Cl.
*A61K 8/00*    (2006.01)

(52) U.S. Cl.
USPC .......................................... 424/59; 424/400

(58) Field of Classification Search
None
See application file for complete search history.

(56) References Cited

U.S. PATENT DOCUMENTS

| 6,936,241 B2 * | 8/2005 | Yamada et al. ............. 424/59 |
| 7,087,650 B2 * | 8/2006 | Lennon ..................... 516/55 |
| 7,214,365 B2 | 5/2007 | Wendel et al. |
| 2004/0253186 A1 | 12/2004 | Maillan et al. |
| 2008/0069898 A1 | 3/2008 | Smith et al. |
| 2013/0045913 A1 | 2/2013 | Germaneau et al. |

FOREIGN PATENT DOCUMENTS

| DE | 10327468 | 1/2005 |
| DE | 102005059742 | 6/2007 |
| EP | 0717313 | 6/1996 |
| EP | 1864648 | 7/2007 |
| EP | 1905483 | 4/2008 |
| EP | 2236173 | 10/2010 |
| EP | 2324819 | 5/2011 |
| FR | 2915387 | 10/2008 |
| FR | 2916346 | 11/2008 |
| FR | 2916347 | 11/2008 |
| FR | 2923385 | 5/2009 |
| FR | 2953715 | 6/2011 |
| WO | WO2005/042828 | 5/2005 |
| WO | WO2006/005846 | 1/2006 |

OTHER PUBLICATIONS

Database GNPD [Online] Mintel: "Rain Water Body Mist", XP002678133, Oct. 2008, Database accession No. 993834.
English Translation of FR2915387A1 obtained Sep. 17, 2013 at http://worldwide.espacenet.com/publicationDetails/originalDocument?CC=FR&NR=2915387A1&KC=A1&FT=D&ND=3&date=20081031&DB=EPODOC&locale=en_EP.

* cited by examiner

*Primary Examiner* — Anand Desai
*Assistant Examiner* — Melissa Mercier
(74) *Attorney, Agent, or Firm* — Hamre, Schumann, Mueller & Larson, P.C.

(57) ABSTRACT

The invention relates to an additive comprising at least 95 wt. % of a mixture consisting of at least one organic filter filtering $UV_A$, at least one organic filter filtering $UV_B$, and from 1 to 50 wt. % of at least one non-volatile oil that is a solvent for said filters. This composition is particularly useful as an agent for protecting the organoleptic properties of a transparent cosmetic composition, against UV radiation.

20 Claims, No Drawings

ANTI-ULTRAVIOLET ADDITIVE COMPRISING A $UV_A$ FILTER, A $UV_B$ FILTER AND AN OIL THAT IS A SOLVENT FOR SAID FILTERS, AND USE THEREOF IN COLOURED AND/OR PERFUMED COMPOSITIONS

The invention relates to a mixture of two organic UV filters dissolved in a non-volatile oil, as well as the use thereof as an anti-ultraviolet additive for protecting coloured and/or perfumed compositions from denaturation by UV radiation.

PRIOR ART

Consumers' attraction for cosmetic products packaged in transparent materials requires no further demonstration. These products are generally transparent themselves and in particular are exposed to light, to ultraviolet radiation (also called "UV radiation" or "UV" in the present application) and to temperature variations.

Now, daylight and UV cause decomposition of the molecules such as perfumes and dyes that these products contain. In particular we may observe a change of the perfume, decoloration, yellowing, pink coloration, flocculation and precipitates of substances, or clouding that may adversely affect the consumer's perception of the product and the efficiency of pumps, when it is packaged in a spray.

For protecting cosmetic compositions packaged in transparent bottles from such degradation throughout their useful life, generally filters that are active against UV (also called "UV filters" in the present application) and an antioxidant system are incorporated in them, in order to guarantee their stability.

It has always been stated in the prior art that the use of two UV filters will not protect a perfume from degradation by UV. Thus, ternary or quaternary mixtures of UV filters have been proposed in order to guarantee stabilization of perfumes.

For example, it was shown in application FR 2 916 346 that the colour and the odour of a toilet water comprising 1 wt. % of a mixture of n-hexyl 2-(4-diethylamino-2-hydroxybenzoyl)benzoate and ethylhexyl methoxycinnamate 35/65 are degraded on exposure to UV and heat, so that it is necessary to add a third UV filter of the butylmethoxy-dibenzoylmethane type to obtain effective protection of the product against UV.

Moreover, the colour and the odour of a toilet water comprising 1 wt. % of ethylhexyl methoxycinnamate and 0.3 wt. % of butylmethoxydibenzoylmethane are degraded on exposure to UV and heat. This is why it was proposed in application WO 2006/005846 to add a third filter, ethylhexyl salicylate, to ethylhexyl methoxycinnamate and butylmethoxydibenzoylmethane to protect cosmetic compositions from decoloration when they are exposed to UV.

Applications FR 2 916 347 and FR 2 923 385 also describe mixtures of filters comprising a cinnamate and a dibenzoylmethane to guarantee stability of the colour and odour of a toilet water. These quaternary mixtures comprise a cinnamate, a dibenzoylmethane and a salicylate derivative, in combination with either a derivative of hydroxyaminobenzophenone, or a derivative of benzotriazole.

However, ethylhexyl salicylate has the drawback of being odorous: it releases a greasy, pyrogenous, plastic, rubbery note, so that its use for stabilization of perfuming solutions is not satisfactory; depending on the percentage at which it is introduced for this application, it may lead to degradation of the authenticity of the perfume.

Finally, it has been proposed to add, to a mixture of UV filters comprising a cinnamate and a dibenzoylmethane, an organic compound comprising a nitroxyl or hydroxylamine group such as tris-tetra-methylhydroxypiperidinol (marketed under the reference Tinogard Q) for protecting fabrics, cosmetic compositions and household maintenance products from the effects of light, heat and oxidation (patent application WO 2005/042828).

Unfortunately the stabilizing additives recommended in the patent applications of the prior art contain large amounts of UV filters, which are raw materials that are expensive and tend to alter the colour or the scent of the perfuming solution.

Increasing the quantity of filters in the perfumes has also been tried, in order to protect the products against UV radiation; however, this route was not successful, because at higher concentrations the film of perfume vaporized on the skin leaves a greasy sensation and because regulatory requirements impose maximum limits to the level of use of each UV filter.

AIM OF THE INVENTION

Therefore there is still a need for new UV-protective additives for cosmetic products containing perfumes and/or dyes that are transparent or translucent, said additives not displaying the drawbacks of the stabilizers of the prior art. Stabilizers that are less expensive and do not alter the organoleptic properties such as the odour and colour of a cosmetic product, while providing sufficient stabilization of the product exposed to daylight or to temperature differences, are therefore sought.

The applicant discovered, surprisingly, that this aim could be achieved by combining two UV filters and a non-volatile, preferably polar, oil.

In contrast to the teaching of the prior art, which suggests using at least three UV filters to obtain sufficient stabilization of perfuming solutions with respect to the adverse influence of UV, the inventors found that it is possible, against all expectations, to use only two UV filters, in a coloured and/or perfumed composition, while guaranteeing sufficient stability of the colour and/or of the perfume. It is also possible to incorporate smaller amounts of UV filters than those recommended in the prior art while guaranteeing sufficient stability. The inventors found, surprisingly, that certain non-volatile oils make it possible to increase the effectiveness of UV filters in a coloured or perfumed composition. These oils in fact improve the solubility of the UV filters, so that it is possible to incorporate them in a smaller amount while guaranteeing sufficient stabilization of the product. The inventors discovered that it is even possible to use only two UV filters for effectively stabilizing a transparent cosmetic product that is exposed to UV.

SUMMARY OF THE INVENTION

The invention relates to an anti-ultraviolet additive comprising at least 95 wt. % of a mixture consisting of:
  at least one organic filter filtering $UV_A$,
  at least one organic filter different from the first, filtering $UV_B$, and
  from 1 to 50 wt. % of at least one non-volatile oil that is a solvent for said filters.
  This oil has the advantage that it is not a UV filter.

The invention also relates to a transparent or translucent composition, for example an alcoholic or aqueous-alcoholic solution, comprising a perfume or a dye and the additive in a sufficient amount to protect the odour or the colour of the composition from degradation by UV radiation.

In one embodiment, the invention relates to a perfuming solution comprising a perfume, at least one volatile alcohol, and the additive in a sufficient amount to protect the odour of the solution from degradation by UV radiation.

The invention also relates to the use of the additive of the invention in a composition, as an agent for protecting its organoleptic properties, in particular the odour and/or colour, against UV.

The invention also relates to a method for stabilizing the organoleptic properties, in particular the colour and/or the odour of a cosmetic composition, characterized in that it consists of incorporating the additive of the invention in the composition.

DETAILED DESCRIPTION OF THE INVENTION

The invention relates firstly to an anti-ultraviolet additive preferably comprising at least 95 wt. % of a mixture consisting of:
 at least one organic filter filtering $UV_A$,
 at least one organic filter filtering $UV_B$, and
 from 1 to 50 wt. % of at least one non-volatile oil that is a solvent for said filters.

The additive is a mixture of compounds that is intended to be incorporated in a cosmetic or dermatological composition. The additive is not intended to be applied as such on keratinous materials, such as the skin, lips, hair, nails, eyelashes or eyebrows.

The additive more preferably comprises at least 97 wt. %, even more preferably at least 99 wt. % of said mixture. According to one embodiment, the additive consists of said mixture.

"Organic UV filter" means any organic compound absorbing UV radiation in the wavelength range from 280 nm to 400 nm. The UV filter is preferably lipophilic, and can be dissolved in the molecular state in an oil, or can be dispersed in an oil in colloidal form or in micellar form.

$UV_A$ means the wavelengths in the range from 315 to 400 nm, and $UV_B$ means the wavelengths in the range from 280 to 315 nm.

According to a preferred embodiment, the additive consists of
 a single organic filter filtering $UV_A$,
 at least one, preferably just one, organic filter filtering $UV_B$, and
 from 1 to 50 wt. % of at least one non-volatile oil that is a solvent for said filters.

According to another embodiment, the additive consists of
 at least one organic filter filtering $UV_A$,
 just one organic filter filtering $UV_B$, and
 from 1 to 50 wt. % of at least one non-volatile oil that is a solvent for said filters.

The invention further relates to an additive consisting of
 a single organic filter filtering $UV_A$,
 a single organic filter filtering $UV_B$, and
 at least one non-volatile oil that is a solvent for said filters.

The additive according to the invention comprises at least two organic UV filters, more preferably at least two lipophilic UV filters, and more preferably at least one lipophilic filter filtering $UV_A$ and at least one lipophilic filter filtering $UV_B$. The additive can alternatively contain a single UV filter filtering $UV_A$ radiation and $UV_B$ radiation.

The additive preferably comprises less than 0.5 wt. %, more preferably less than 0.2 wt. % of inorganic sun filter(s) relative to the total weight of the additive. The additive of the invention is preferably free from inorganic sun filters.

The total amount of sun filter(s) in the additive is preferably between 70 and 98 wt. %, more preferably between 80 and 90 wt. % relative to the total weight of the additive.

An organic filter active in the $UV_A$ is advantageously selected from:
 dibenzoylmethane derivatives,
 menthyl anthranilate notably sold under the reference NEO HELIOPAN® MA by SYMRISE,
 mixtures thereof.

Among the UV filters derived from dibenzoylmethane, we may notably mention, non-exhaustively: 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane. Among the dibenzoylmethane derivatives mentioned above, quite particularly 4-(tert-butyl)-4'-methoxy dibenzoylmethane will be used, also called butyl methoxy dibenzoylmethane (abbreviated to BMDBM, with the INCI name 1-[4-(1,1-dimethylethyl)phenyl]-3-(4-methoxyphenyl)-1,3-propanedione and with the USAN name azobenzone) offered for sale under the trade names PARSOL 1789 from the company DSM NUTRITIONAL PRODUCTS, or EUSOLEX 9020 from the company MERCK.

The filter active in the $UV_B$ can be selected from:
 salicylic derivatives: Homosalate notably sold under the name NEO HELIOPAN® HMS; ethylhexyl salicylate notably sold under the name NEO HELIOPAN® OS by SYMRISE; octyl salicylate notably sold under the name NEO HELIOPAN® type 05;
 cinnamate derivatives;
 derivatives of benzylidene camphor: 3-benzylidene camphor manufactured under the name MEXORYL® SD by CHIMEX; methylbenzylidene camphor notably sold under the name NEO HELIOPAN® MBC;
 triazine derivatives: ethylhexyltriazone notably sold under the trade name UVINUL® T150 by BASF, Diethylhexyl Butamido Triazone sold under the trade name UVASORB® HEB, Bis Ethylhexyloxyphenol Methoxyphenyl Triazine;
 para-aminobenzoates, such as Ethyl PABA; Ethyl Dihydroxypropyl PABA; Ethylhexyl Dimethyl PABA (ESCALOL® 507 from ISP);
 derivatives of imidazolines: Ethylhexyl Dimethoxybenzylidene Dioxoimidazoline Propionate;
 derivatives of benzal malonate: polyorganosiloxanes with a benzal malonate function such as Polysilicone-15 notably sold under the trade name PARSOL® SLX by DSM Nutritional Products Inc.; dineopentyl-4'-methoxybenzalmalonate;
 and mixtures thereof.

Among the cinnamate derivatives, we may notably mention non-exhaustively: ethyl-2-hexyl-p-methoxycinnamate, isopropyl-p-methoxycinnamate, isoamyl methoxycinnamate, cinoxate (2-ethoxyethyl-p-methoxycinnamate), diethanolamine methoxycinnamate, glyceryl ethyl-2-hexanoate di-p-methoxycinnamate, [4-bis(trimethylsiloxy)methylsilyl-3-methylbutyl]-3,4,5-trimethoxycinnamate.

Among the cinnamate derivatives mentioned above, ethyl-2-hexyl-p-methoxycinnamate will be used quite particularly, which is also called ethylhexyl methoxycinnamate or octyl methoxycinnamate (USAN name: octinoxate) offered for sale under the trade names PARSOL MCX from the company DSM NUTRITIONAL PRODUCTS, UVINUL MC 80 from the company BASF, and Uvinul A+B from the company BASF.

The filter active in the $UV_A$ can be selected from filters that are active both in the $UV_A$ and in the $UV_B$, such as:
- benzophenone derivatives: benzophenone-1 sold under the trade name UVINUL® 400; benzophenone-2 sold under the trade name UVINUL D50; benzophenone-3 or oxybenzone sold under the trade name UVINUL® M40; benzophenone-4 sold under the trade name UVINUL® MS40; benzophenone-6 sold under the trade name HELISORB 11; benzophenone-8 sold under the trade name SPECTRASORB® UV-24;
- phenylbenzotriazole derivatives: Drometrizole Trisiloxane notably sold under the name Silatrizole® by RHODIA CHIMIE; Methylene bis-Benzotriazolyl Tetramethylbutylphenol sold in solid form notably under the trade name MIXXIM® BB/100 by FAIRMOUNT CHEMICAL;
- bis-resorcinyltriazine derivatives: Bis-Ethylhexyloxyphenol Methoxyphenyl Triazine notably sold under the trade name TINOSORB® S by CIBA GEIGY;
- benzoxazole derivatives: 2,4-bis-[5-1-(dimethylpropyl) benzoxazol-2-yl-(4-phenyl)-imino]-6-(2-ethylhexyl)-imino-1,3,5-triazine notably sold under the name Uvasorb® K2A by Sigma 3V;
- and mixtures thereof.

The filter active in the $UV_B$ is different from the filter active in the $UV_A$ and can be selected independently of said filter, from the filters that are active both in the $UV_A$ and in the $UV_B$ described above.

The $UV_A$ and $UV_B$ filters are combined in the additive so as to cover effectively the whole spectrum of UV radiation defined above. The content of each of the two filters is set as a function of their ability to stop UV radiation.

According to one embodiment, the additive contains at least one $UV_A$ filter selected from dibenzoylmethane derivatives, and at least one $UV_B$ filter selected from cinnamate derivatives.

The UV filter selected from cinnamate derivatives advantageously represents from 20 to 90 wt. %, preferably from 30 to 75 wt. %, of the weight of the additive.

The UV filter selected from cinnamate derivatives advantageously represents from 0.3 to 0.4 wt. % of the weight of the coloured and/or perfumed composition.

The UV filter selected from dibenzoylmethane derivatives advantageously represents from 5 to 75 wt. %, preferably from 10 to 55 wt. %, of the weight of the additive.

The UV filter selected from dibenzoylmethane derivatives advantageously represents from 0.05 to 0.1 wt. % of the weight of the coloured and/or perfumed composition.

The additive of the invention can advantageously contain an organic filter that is solid at 25° C. and 0.1 MPa. The invention more particularly finds interest in the formulation of a solid lipophilic UV filter, for example
- 2,4-bis[[4-(2-ethylhexyloxy)-2-hydroxy]phenyl]-6-(4-methoxyphenyl)-1,3,5-triazine notably marketed under the reference Tinosorb S®,
- 2,2-methanediylbis[6-(2H-benzotriazol-2-yl)-4-(2,4,4-trimethylpentan-2-yl)phenol] also called methylene bis-benzotriazolyl tetrabutylphenol or Bisoctrizole notably marketed under the reference Tinosorb M®,
- 2,4,6-trianilino-(p-carbo-2'-ethylhexyl-1'-oxy)-1,3,5-triazine notably marketed under the reference Uvinul® T 150 by BASF,
- dibenzoylmethane derivatives,
- the benzotriazole derivatives described in patent application EP 0717313.

The additive of the invention can advantageously also contain a salicylate filter.

The additive of the invention contains a non-volatile oil that dissolves the organic UV filters, and advantageously increases their degree of absorption of UV radiation.

"Oil" means, in the sense of the invention, a fat that is insoluble in water, and is liquid at 25° C. and 0.1 MPa. "Non-volatile oil" means any oil having a vapour pressure, at 25° C. and 0.1 MPa, that is non-zero and is less than 2.6 Pa, preferably less than 0.13 Pa. In the sense of the present invention, a non-volatile oil is not a perfume and is not an organic UV filter. According to a preferred embodiment, the non-volatile oil is different from any organic UV filter that has been previously described.

The non-volatile oil is advantageously miscible in the continuous phase of a composition or in a solvent, in which the additive of the invention is dispersed or dissolved. The miscibility of the non-volatile oil in a solvent or a phase can be evaluated according to the following protocol. The selected solvent or phase (80 wt. %) is weighed in a beaker, then the non-volatile oil selected (20 wt. %) is added to the beaker. It is stirred for 5 minutes and then the whole is packaged in a 120-ml pill box. It is left to stand for 24 hours at 25° C. After standing for 24 hours, if the mixture is visually clear and homogeneous, it is considered that the non-volatile oil is miscible in the solvent or in the continuous phase.

According to one embodiment, the oil is a hydrocarbon oil comprising at most one aliphatic ring. The oil is preferably an aliphatic oil, i.e. it is not aromatic in the sense that it does not contain a cyclic system obeying Hückel's aromaticity rule.

"Aliphatic" means a non-aromatic compound. "Aliphatic ester, ether, alcohol or acid" means a compound consisting of carbon atoms, of hydrogen atoms and of a COO, COC, OH or COOH group, respectively. "Hydroxylated aliphatic ester" means a hydrocarbon compound comprising a COO group and at least one OH group, preferably a single OH group.

According to another embodiment, the oil is a silicone oil comprising at least one aromatic carbon-containing group.

"Aliphatic ester" means a compound consisting of carbon atoms, of hydrogen atoms and of at least one COO group. "Monoester" means a compound comprising one COO group, and "diester" means a compound comprising two COO groups.

"Hydroxylated ester" means a compound comprising at least one COO group and at least one OH group.

In another embodiment, an ester selected from aliphatic monoesters and diesters is preferred. The hydroxylated esters are preferably non-aromatic.

The non-volatile oil is preferably selected from aliphatic mono- and diesters, non-hydroxylated aromatic esters, aliphatic carbonates and phenylated silicones.

As oils usable in the additive of the invention, we may mention for example:
- aliphatic mono- and diesters, notably i) monoesters of a linear or branched, saturated or unsaturated, preferably saturated, aliphatic carboxylic acid comprising 8 to 20 carbon atoms, and of an aliphatic monohydric alcohol comprising 3 to 20 carbon atoms, ii) aliphatic diesters of an aliphatic dicarboxylic acid comprising 4 to 10 carbon atoms and of a monohydric alcohol, monoesters of benzoic acid and of an aliphatic alcohol comprising 8 to 20 carbon atoms, ethyl-2-hexyl benzoate, octyl-2-dodecyl benzoate, isostearyl benzoate, $C_{12}$-$C_{15}$ alkylbenzoate, tri- and tetra-esters such as esters of pentaerythritol, notably pentaerythrityl tetraisostearate, esters of trimethylolpropane, notably trimethylolpropane triisostearate, esters of citric acid, notably tridecyl citrate, and tridecyl trimellitate, dialkyl carbonates whose alkyl groups contain from 8 to 18 carbon atoms such as dicaprylyl carbonate, di(ethyl-2-hexyl)-carbonate, hydroxylated aliphatic mono- or diesters such as i) esters of a hydroxylated aliphatic mono- or dicarboxylic acid comprising 3 to 20 carbon atoms, and of an aliphatic monohydric alcohol comprising 6 to 20 carbon atoms, for example isostearyl lactate, octyl hydroxystearate, octyldodecyl hydroxystearate, cetyl lactate, myristyl lactate, diisostearyl malate, or ii) aliphatic mono- and diesters of polyols, in particular of diols and triols, such as esters of an aliphatic monocarboxylic acid comprising 3 to 20 carbon atoms, and of an aliphatic diol or triol comprising 3 to 20 carbon atoms, hydroxylated aromatic mono- and diesters of a hydroxylated aromatic carboxylic acid and of an aliphatic monohydric alcohol comprising at least 10 carbon atoms, saturated or unsaturated aliphatic alcohols having from 8 to 26 carbon atoms, such as octyldodecanol, octyldecanol, 2-butyloctanol, 2-hexyldecanol, 2-undecylpentadecanol, saturated or unsaturated aliphatic monocarboxylic acids having from 7 to 29 carbon atoms such as oleic acid, linoleic acid, linolenic acid or isostearic acid, silicone oils having at least one alkoxy or phenyl group, pendant or at the end of the silicone chain, having from 2 to 24 carbon atoms, notably phenyltrimethicone, phenyldimethicones, phenyltrimethylsiloxydiphenylsiloxanes, diphenyl dimethicones, diphenylmethyldiphenyl trisiloxanes, 2-phenylethyltrimethylsiloxysilicates, and polymethylphenylsiloxanes;

glycols, aliphatic ethers comprising more than 10 carbon atoms, and mixtures thereof.

In one embodiment, the non-volatile oil is preferably an ester selected from aliphatic monoesters and diesters.

According to another embodiment, the oil is a silicone oil comprising aromatic carbon-containing groups.

Among the aliphatic mono- and diesters, esters are preferred comprising 10 to 25 carbon atoms, preferably from 14 to 22 carbon atoms, for example esters of isononanoic acid such as isononyl isononanoate, isodecyl isononanoate, decyl-2-hexyl isononanoate, isostearyl isononanoate, cetearyl isononanoate, tridecyl isononanoate. We may also mention isopropyl myristate, ethyl-2-hexyl palmitate, octyl-2-dodecyl stearate, octyl-2-dodecyl erucate, isostearyl isostearate, octyl dodecyl stearoyl stearate, isostearyl palmitate, isocetyl stearate, octyldodecyl myristate, triisostearyl trilinoleate, octyldodecyl neodecanoate, octyldodecyl octanoate, isobutyl stearate, isodecyl neopentanoate, octyldodecyl neopentanoate, ethyl-2-hexyl isostearate, butyl isostearate, isopropyl palmitate, stearyl heptanoate, isopropyl stearate, isostearyl neopentanoate, isopropyl isostearate, cetyl octanoate (or palmityl octanoate), butyl stearate, hexyl laurate (or hexyl dodecanoate), ethyl laurate, decyl oleate, oleyl oleate, myristyl myristate, hexyldecyl dimethyloctanoate, isocetyl isostearate, hexyl-2-decyl myristate, heptyl-2-undecyl palmitate, cetyl 2-ethyl hexanoate.

Among the esters of dicarboxylic acids, we may also mention di(ethyl-2-hexyl) sebacate, diisopropyl sebacate, di(ethyl-2-hexyl)succinate, di(hexyl-2-decyl)adipate, di(heptyl-2-undecyl)adipate.

Among the polyol mono- and diesters, we may mention the diesters of alkylene glycol with an aliphatic acid having from 6 to 20 carbon atoms, such as propylene glycol dioctanoate, neopentyl glycol diheptanoate and diethylene glycol diisononanoate; butylene glycol dicaprate/dicaprylate, propylene glycol dicaprate/dicaprylate, neopentyl glycol dicaprate, diethylene glycol diisononanoate, propylene glycol diisostearate, propylene glycol dipelargonate, propylene glycol dioctanoate, neopentyl glycol diheptanoate, tripropylene glycol dipivalate; and mono-alkanoates of glyceryl such as glyceryl heptanoate, glyceryl octanoate, and glyceryl decanoate.

The non-volatile oil preferably represents from 5 to 30 wt. % of the additive. More preferably it represents from 10 to 20 wt. % of the weight of the additive, notably about 15 wt. %.

Advantageously the additive comprises at most two UV filters.

A preferred additive consists of octyl methoxycinnamate, butyl methoxy-dibenzoylmethane and a non-volatile oil selected from the group comprising diisostearyl malate, phenyl trimethicone, butylene glycol dicaprylate/dicaprate, $C_{12}$-$C_{15}$-alkylbenzoate and isononyl isononanoate.

A more preferred additive consists of octyl methoxycinnamate, butyl methoxy-dibenzoylmethane and butylene glycol dicaprylate/dicaprate. The octyl methoxycinnamate represents advantageously from 60 to 80% by weight of the additive. The butyl methoxy-dibenzoylmethane represents advantageously from 10 to 20% by weight of the additive, and the butylene glycol dicaprylate/dicaprate represents advantageously from 10 to 20% by weight of the additive.

The invention relates secondly to a transparent or translucent composition comprising a perfume and/or a dye, and an additive consisting of at least one organic $UV_A$ filter, at least one organic $UV_B$ filter, and at least one non-volatile oil that is a solvent for said filters, the additive being in a sufficient amount for protecting the odour and/or the colour of the composition from degradation by UV radiation.

The composition preferably contains from 0.1 to 5 wt. %, preferably from 0.3 to 3 wt. %, and more preferably from 0.5 to 1 wt. % of the additive describes above.

In the composition of the invention, the organic filters can represent from 0.1 to 3.5 wt. %, more preferably from 0.5 to 2 wt. %, of the weight of the composition. The composition of the invention is not used to protect the skin from UV rays. The quantity of UV filters used is well below the necessary doses that are efficient to protect the skin or the lips.

The composition is advantageously translucent or transparent in its bulk, and it is notably put in packaging that is itself transparent or translucent, when it is offered for sale. The term "translucent" signifies "which allows light to pass through, but does not allow objects to be distinguished". The term "transparent" signifies "which allows light to pass through, and makes it possible to distinguish objects".

The composition can be a make-up product or a care product, such as a styling gel, a shampoo, a lip gloss, or a nail varnish.

The invention also relates to a perfuming solution comprising at least one volatile alcohol, a perfume and an additive consisting of at least one organic $UV_A$ filter, at least one organic $UV_B$ filter, and at least one non-volatile oil soluble in said alcohol and a solvent for said filters, the additive being in a sufficient amount for protecting the perfuming solution from degradation by UV radiation.

"Perfuming solution" means a composition containing, as main ingredient, an alcohol in which a perfume is dissolved in a sufficient amount for perfuming keratinous materials. Water-in-oil and oil-in-water emulsions are excluded from this definition. The solution is advantageously translucent or transparent, which makes protection thereof against visible light and UV radiation even more necessary. The perfuming solution is notably in the form of aqueous-alcoholic solution.

The perfuming solution can be in the form of fresh water, toilet water, perfume water, aftershave lotion, make-up removing lotion, or care water.

The transparent or translucent composition of the present invention can contain at least one volatile alcohol.

"Volatile alcohol" means, in the sense of the invention, any compound comprising at least one alcohol function notably having a vapour pressure, at 25° C. and 0.1 MPa, in the range from 0.13 to 40 000 Pa, preferably from 1.3 to 13 000 Pa, more preferably from 1.3 to 8000 Pa, for example greater than 2000 Pa.

The volatile alcohols are preferably selected from monohydric alcohols having from 1 to 5 carbon atoms and can be selected from methanol, ethanol, propanol, isopropanol, n-butanol, isobutanol and t-butanol.

The volatile alcohol or alcohols are preferably present in amounts in the range from 40 to 95 wt. % and more preferably in amounts in the range from 55 to 80 wt. % relative to the total weight of the composition.

According to a preferred embodiment, the composition is a perfuming solution containing a volatile alcohol and water in an amount in the range from 0.01 to 20 wt. %, preferably from 0.1 to 15 wt. %, and more preferably from 0.2 to 12 wt. % relative to the total weight of the solution.

In this embodiment, the non-volatile oil is preferably soluble at 25° C. in at least one aliphatic monohydric alcohol comprising 2 to 5 carbon atoms.

The solubility of the non-volatile oil in alcohol can be assessed by the protocol for measurement of miscibility as described above.

The composition preferably contains from 0.01 to 10 wt. %, more preferably from 0.1 to 5 wt. %, and more preferably from 0.3 to 2 wt. % of the additive described above containing UV filters dissolved in a non-volatile oil.

The composition can contain a perfume, defined as an odorous substance or a mixture of odorous substances that can evaporate at 25° C.

The additive according to the invention can protect the perfume from degradation by UV, when the composition contains it.

Each perfume has what is called a top note, which is the odour that diffuses first on applying the perfume or on opening its container, a middle note which corresponds to the complete perfume (emission for some hours after the top note) and a basic note, which is the most persistent odour (emission for several hours after the middle note). The persistence of the basic note corresponds to the odour persistence of the perfume. The perfume can for example be selected from compounds whose INCI name appearing in the list of ingredients of the composition offered for sale is "Perfume". A perfume is a compound that is at least partially volatile at room temperature, the odour of which is detected.

"Perfume" also means any organic compound that is able to perfume the skin, hair, scalp, lips or nails.

The amount of perfume will more preferably be from 3 to 50 wt. %, better still from 5 to 30 wt. %, even better from 10 to 20 wt. % relative to the total weight of the composition.

Perfumes and aromas of natural or synthetic origin and mixtures thereof can be used. As perfumes and aromas of natural origin, we may mention for example extracts from flowers (lily, lavender, rose, jasmine, ylang-ylang), from stems and leaves (patchouli, geranium, petitgrain), from fruits (coriander, anise, cumin, juniper), from the rind of fruits (bergamot, lemon, orange), from roots (angelica, celery, cardamom, iris, sweet rush), from wood (pine wood, sandalwood, guaiacum, pink cedar), from herbs and grasses (tarragon, lemon grass, sage, thyme), from needles and branches (spruce, fir, pine, dwarf pine), from resins and balsams (galbanum, elemi, benzoin, myrrh, olibanum, opopanax).

As perfume of synthetic origin, we may mention for example benzyl acetate, benzyl benzoate, phenoxyethyl isobutyrate, p-tert-butylcyclohexyl acetate, citronellyl acetate, citronellyl formate, geranyl acetate, linalyl acetate, dimethyl-benzylcarbinyl acetate, phenylethyl acetate, linalyl benzoate, benzyl formate, ethylmethylphenyl glycinate, alkylcyclohexyl propionate, styralyl propionate and benzyl salicylate, benzylethyl ether, linear alkanals having from 8 to 18 carbon atoms, citral, citronellal, citronellyloxyacetaldehyde, cyclamenaldehyde, hydroxycitronellal, lilial and bourgeonal, ionones such as alpha-isomethylionone, and methylcedryl ketone, anethole, citronellol, eugenol, isoeugenol, geraniol, linalol, phenylethyl alcohol, terpineol, terpenes. These compounds are often in the form of a mixture of two or more of these odorous substances.

Moreover, it is also possible to use essential oils, components of aromas, for example essences of sage, of chamomile, of clove, of lemon balm, of mint, of cinnamon tree leaves, of lime blossom, of juniper, of vetiver, of olibanum, of galbanum, of labolanum and of lavandin.

Preferably the following are used as perfume, alone or mixed: bergamot essence, dihydromyrcenol, filial, lyral, citronellol, phenylethyl alcohol, alpha-hexylcinnamaldehyde, geraniol, benzylacetone, cyclamenaldehyde, linalol, ambroxan, indole, hedione, sandelice, essences of lemon, of mandarin and of orange, allyl amine glycolate, cyclovertal, essence of lavandin, essence of sage, betadamascone, essence of geranium, cyclohexyl salicylate, phenylacetic acid, geranyl acetate, benzyl acetate, rose oxide.

Among the known olfactory notes, we may mention for example hesperides perfumes, aromatics, floral perfumes, musks, fruity perfumes, spicy perfumes, oriental perfumes, marine perfumes, aquatic notes, chypre perfumes, woody perfumes, ferns and mixtures thereof.

The perfume can also contain triethyl citrate as solvent and/or diluent.

The perfume generally represents from 5 to 40 wt. %, preferably from 10 to 30 wt. % of the weight of the composition of the invention.

The composition according to the invention can comprise at least one dye such as fat-soluble dyes, water-soluble dyes or dyes soluble in an aqueous-alcoholic solution.

The additive according to the invention can play a role of protection of the dyes, in order to avoid any degradation of colour connected directly with their reaction to light or to temperature, or to interaction of these dyes with other ingredients of the composition such as perfumes or active agents, when the composition is exposed to light or heat.

The dyes that are water-soluble or soluble in an aqueous-alcoholic solution are for example: caramel, Yellow 5, Acid Blue 9/Blue 1, Green 5, Green 3/Fast Green FCF 3, Orange 4, Red 4/Food Red 1, Yellow 6, Acid Red 33/Food Red 12, Red 40, carmine (CI 15850, CI-75470), Ext. Violet 2, Red 6-7, Ferric Ferrocyanide, Ultramarines, Acid Yellow 3/Yellow 10, Acid Blue 3, Yellow 10. The fat-soluble dyes are for example Sudan Red, D&C Red 17, D&C Green 6, beta-carotene, soya oil, Sudan Brown, D&C Yellow 11, D&C Violet 2, D&C Orange 5, quinoline yellow, annatto.

The dyes generally represent from 0.01 to 1 wt. %, preferably from 0.05 to 0.5 wt. % of the weight of the composition.

The composition according to the invention can be packaged in transparent materials such as bottles. It can also be packaged in pressurized devices. These devices are well known by a person skilled in the art and comprise non-aerosol pumps or "atomizers", aerosol containers comprising a propellant as well as aerosol pumps using compressed air as propellant. The compositions packaged in aerosols according to the invention generally contain conventional propellants such as for example hydrofluorinated compounds, dichlorodifluoromethane, difluoroethane, dimethyl ether, isobutane, n-butane, propane, trichlorofluoromethane.

The invention relates thirdly to the use of the additive described above as an agent for protecting the organoleptic properties of a composition against UV radiation, said composition being characterized in that it contains at least one dye and/or perfume, and from 0.1 to 5 wt. %, preferably from 0.3 to 3 wt. %, and more preferably from 0.5 to 1 wt. % of said additive.

The composition is advantageously a cosmetic composition for care or make-up of the skin, or a perfuming solution. It is preferably transparent or translucent.

The cosmetic composition can for example be a serum, a lotion, a cream (oil-in-water emulsion), a hydrogel, preferably a mask, or can also be in the form of a stick or a balm, a patch, or in the form of a make-up product of the lipstick type, mascara or foundation.

The cosmetic composition can advantageously comprise at least one cosmetically acceptable active agent, in the form of purified molecules and/or extracts, notably plant extracts.

Advantageously, the cosmetic composition can also further comprise at least one cosmetically acceptable excipient that can be selected from pigments, polymers, surfactants, rheology agents, electrolytes, pH adjusters, antioxidants, preservatives, solvents—optionally volatile—, and any mixture thereof.

Among the antioxidants, we may mention for example ascorbic acid, di-tert-butyl-p-hydroxytoluene (also called BHT or 2,6-di-tert-butyl-p-cresol), BHA (tert-butyl-4-hydroxyanisole), tocopherols such as vitamin E, derivatives of tocopherol such as tocopheryl acetate, gallic acid and derivatives thereof.

The cosmetic composition can in particular advantageously comprise at least one volatile solvent that can notably be selected from the volatile alcohols, preferably selected from monohydric alcohols having from 1 to 5 carbon atoms, volatile silicone oils, such as octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane, decamethyltetrasiloxane, isododecane, octamethylcyclotetrasiloxane, decamethylcyclopentasiloxane, dodecamethylcyclohexasiloxane, heptamethylhexyltrisiloxane, heptamethyloctyltrisiloxane, octamethyltrisiloxane, decamethyltetrasiloxane, and mixtures thereof, or else ethyl acetate.

The invention further relates to the use of an additive as described above as an agent for protecting the organoleptic properties of a composition against UV radiation, said composition being characterized in that it contains at least one dye and/or perfume, and from 0.1 to 5 wt. %, preferably from 0.3 to 3 wt. %, and more preferably from 0.5 to 1 wt. % of said additive.

The composition is preferably a cosmetic composition for care or make-up of the skin or a perfuming solution, notably a transparent or translucent composition.

The characteristic features described in relation to the composition and the additive are applicable to the use of the additive according to the invention.

Other aims, features and advantages of the invention will become clear to a person skilled in the art on reading the examples, which are given purely as illustration and therefore will not in any way limit the scope of the invention. The examples form an integral part of the present invention and are thus of general application.

Moreover, in the following examples, all percentages are given by weight, temperature is expressed in degrees Celsius unless stated otherwise, and pressure is atmospheric pressure.

EXAMPLE 1

Perfuming Solutions

A—Preparation of Perfuming Solution

Perfuming solutions, also called fragrances, were prepared with the following composition:

TABLE 1

|  | Fragrance No. 1 | Fragrance No. 2 | Fragrance No. 3 |
| --- | --- | --- | --- |
| Alcohol at 96.2 vol. % | Q.s. 100 | Q.s. 100 | Q.s. 100 |
| Concentrate | 11.00 of concentrate No. 1 | 17.85 of concentrate No. 2 | 30.00 of concentrate No. 3 |
| Purified water | 10.38 | 2.54 | 0.56 |
| dyes | 0.11 | 0.10 | 0.43 |
| BHT | $5 \times 10^{-3}$ | $5 \times 10^{-3}$ | $1 \times 10^{-2}$ |

Concentrate No. 1 was composed predominantly of hedione, concentrate No. 2 was composed predominantly of rose essence, and concentrate No. 3 was composed predominantly of jasmine absolute. A mixture of filters and of non-volatile oil according to the invention, having one of the following four compositions, was incorporated in each of these fragrances:

TABLE 2

|  | Mixture 1 | Mixture 2 | Mixture 3 | Mixture 4 |
| --- | --- | --- | --- | --- |
|  | 70% OCTYL METHOXYCINNAMATE 15% BMDBM* | | | |
| DIISOSTEARYL MALATE | 15% | | | |
| PHENYL TRIMETHICONE | | 15% | | |
| BUTYLENE GLYCOL DICAPRYLATE/ DICAPRATE | | | 15% | |
| ISONONYL ISONONANOATE | | | | 15% |

*BMDBM: 4-(tert-butyl)-4'-methoxy dibenzoylmethane

The ethanol and the water were mixed cold in a beaker with Ystral stirring for 5 min. Then the dyes were added, in the form of a solution in ethanol or in water as appropriate, to the aqueous-alcoholic mixture, and it was stirred for 5 minutes.

The antioxidant BHT, BMDBM, octyl methoxycinnamate and the non-volatile oil were mixed in a dish at 70° C. with magnetic stirring, varying the amount of the mixture in the fragrance between 0.1 and 5 wt. %.

Then the mixture was left to cool and the perfume was added, with magnetic stirring. The contents of the dish were then mixed with the coloured aqueous-alcoholic solution with stirring for 10 min, packaged in a perfume atomizer for testing sprayability, in 30-ml pill boxes filled with 25 ml for stove stabilities, then in 60-ml glass bottles for the SUN TEST and olfactory testing.

B—Stability and Sensory Assessment of the Perfuming Solutions

We then evaluated the thermal stability, cold stability and stability to UV radiation of each of the three fragrances containing one of the four additives described above, according to the following protocols.

Stability of Homogeneity of the Solution in a Stove at 4° C. and 45° C.

The 30-ml pill boxes, filled to 25 ml with a fragrance, are put in a stove at 45° C. and in a refrigerator at 4° C. for 3 months. The solution is stable (compliant result) if there is no phase separation or clouding or significant deposit.

Stability of the Colour and of the Odour to UV

The $L^*a^*b^*$ colour coordinates of the mixture, placed in a 60-ml glass bottle filled to 55 ml with a fragrance, were measured before irradiation by means of a Minolta 3600D CM, POS 0118 spectro-colorimeter.

The bottles, each containing one fragrance, are placed upright, which permits complete exposure of the bottle to UV, for 12 hours in the following conditions.

Each sample is irradiated in a Suntest™ apparatus, model CPS. The UV source used is a xenon lamp emitting between 300 and 800 nm at a power of 765 $W/m^2$. The xenon lamp is associated with a "short cut-off" quartz filter combined with "UV Special Glass". The sample is maintained at a temperature of 25° C. (using cooling and/or air conditioning plates).

After 12 hours of irradiation, the $L^*a^*b^*$ coordinates of the fragrance containing the additive were measured again. The colour of the solution is considered stable (compliant result) if the difference between the two measurements in standard conditions of measurement ($D_{65}$ illuminant and Observer at 10°), expressed by delta E, is less than 5, preferably less than 1.

The odour of the solution before and after exposure to UV radiation in the conditions described above was also evaluated by olfactory experts.

The test result is deemed compliant if the olfactory expert does not detect any significant difference in intensity of odour after exposure to UV radiation.

Greasy Sensation Left on the Skin (Sensory Assessment)

The fragrance was applied on the neck by spraying with an atomizer, and the aim was to detect any residual greasy sensation left on the skin, once the alcohol and water had evaporated.

Assessment is based on residual greasy sensation on the skin, or on visual observations (residual greasy film or clothing stained).

For example, a solution containing fragrance No. 2 and 10 wt. % of mixture 2, 3 or 4 is judged too greasy by the expert.

The test result is deemed compliant if the expert does not detect an uncomfortable sensation and there is no observation of greasiness.

The results of these various assessments are reported in Tables 3 to 8 below. The statements in parentheses qualify the result obtained without altering its compliance. The statements in italics characterize observations that make the result non-compliant.

TABLE 3

| Fragrance No. 2 + X % of Additive | | Additive 1 | Additive 2 | Additive 3 | Additive 4 |
|---|---|---|---|---|---|
| 0.1 STOVE STABILITY | 4° C. | Compliant | Compliant | Compliant | Compliant |
| | 45° C. | Compliant | Compliant | Compliant | Compliant |
| SUN TEST 12 H | | Compliant | Compliant | Compliant | Compliant |
| SENSORY ASSESSMENT | | Compliant | Compliant | Compliant | Compliant |
| OLFACTORY TEST AFTER 12 H OF SUNTEST | | Olfactory note compliant | Olfactory note compliant | Olfactory note compliant | Olfactory note compliant |
| 0.5 STOVE STABILITY | 4° C. | Compliant | Compliant | Compliant | Compliant |
| | 45° C. | Compliant | Compliant | Compliant | Compliant |
| SUN TEST 12 H | | Compliant | Compliant | Compliant | Compliant |
| SENSORY ASSESSMENT | | Compliant | Compliant | Compliant | Compliant |
| OLFACTORY TEST AFTER 12 H OF SUNTEST | | Olfactory note compliant | Olfactory note compliant | Olfactory note compliant | Olfactory note compliant |
| 1 STOVE STABILITY | 4° C. | Compliant | Compliant | Compliant | Compliant |
| | 45° C. | Compliant | Compliant | Compliant | Compliant |
| SUN TEST 12 H | | Compliant | Compliant | Compliant | Compliant |
| SENSORY ASSESSMENT | | Compliant | Compliant | Compliant | Compliant |
| OLFACTORY TEST AFTER 12 H OF SUNTEST | | Olfactory note compliant | Olfactory note compliant | Olfactory note compliant | Olfactory note compliant |
| 5 STOVE STABILITY | 4° C. | Compliant | Compliant | Compliant | Compliant |
| | 45° C. | Compliant | Compliant | Compliant | Compliant |
| SUN TEST 12 H | | Compliant | Compliant | Compliant | Compliant |
| SENSORY ASSESSMENT | | Compliant (slightly greasy) | Compliant (slightly greasy) | Compliant (slightly greasy) | Compliant (slightly greasy) |
| OLFACTORY TEST AFTER 12 H OF SUNTEST | | Olfactory note compliant (slight loss of intensity). | Olfactory note compliant (slight loss of intensity). | Olfactory note compliant (slight loss of intensity). | Olfactory note compliant (slight loss of intensity). |

TABLE 4

|  |  | Fragrance No. 1 | Fragrance No. 1 + 0.5% Additive 1 | Fragrance No. 1 + 0.5% Additive 2 | Fragrance No. 1 + 0.5% Additive 3 | Fragrance No. 1 + 0.5% Additive 4 |
| --- | --- | --- | --- | --- | --- | --- |
| STOVE STABILITIES | 45° C. | Compliant | Compliant | Compliant | Compliant | compliant |
|  | 4° C. | Compliant | Compliant | Compliant | Compliant | compliant |
| SUN TEST 12 H |  | complete decoloration | Compliant (slightly pinkish) | Compliant (slightly pinkish) | Compliant (slightly pinkish) | Compliant (slightly pinkish) |
| SENSORY ASSESSMENT |  | — | Compliant (no greasy effect on the skin) | Compliant (no greasy effect on the skin) | Compliant (no greasy effect on the skin) | Compliant (no greasy effect on the skin) |
| OLFACTORY TEST AFTER 12 H OF SUN TEST |  | Loss of intensity of the olfactory note | Olfactory note compliant | Olfactory note compliant | Olfactory note compliant | Olfactory note compliant |

TABLE 5

|  |  | Fragrance No. 3 | Fragrance No. 3 + 1% Additive 1 | Fragrance No. 3 + 1% Additive 2 | Fragrance No. 3 + 1% Additive 3 | Fragrance No. 3 + 1% Additive 4 |
| --- | --- | --- | --- | --- | --- | --- |
| STOVE STABILITIES | 45° C. | Compliant | Compliant | Compliant | Compliant | Compliant |
|  | 4° C. | Compliant (very slight wisps) | Compliant | Compliant | Compliant | Compliant |
| SUN TEST 12 H |  | complete decoloration | Compliant (slightly decoloured) | Compliant (slightly decoloured) | Compliant (slightly decoloured) | Compliant (slightly decoloured) |
| SENSORY ASSESSMENT |  | — | Compliant (No greasy effect on the skin) | Compliant (no greasy effect on the skin) | Compliant (no greasy effect on the skin) | Compliant (no greasy effect on the skin) |
| OLFACTORY TEST AFTER 12 H OF SUN TEST |  | Loss of intensity of the olfactory note | Olfactory note compliant | Olfactory note compliant | Olfactory note compliant | Olfactory note compliant |

TABLE 6

|  |  | Fragrance No. 1 + 5% Additive 1 | Fragrance No. 1 + 5% Additive 2 | Fragrance No. 1 + 5% Additive 3 | Fragrance No. 1 + 5% Additive 4 |
| --- | --- | --- | --- | --- | --- |
| STOVE STABILITIES | 45° C. | Compliant | Compliant | Compliant | Compliant |
|  | 4° C. | Compliant | Compliant | Compliant | Compliant |
| SUN TEST 12 H |  | Compliant (slight yellowing) | Compliant (slight yellowing) | Compliant (slight yellowing) | Compliant (slight yellowing) |
| SENSORY ASSESSMENT |  | Compliant (slightly greasy) | Compliant (slightly greasy) | compliant (slightly greasy) | Compliant (slightly greasy) |
| OLFACTORY AFTER 12 H OF SUN TEST |  | Olfactory note compliant (slight loss of intensity). | Olfactory note compliant (slight loss of intensity). | Olfactory note compliant (slight loss of intensity). | Olfactory note compliant (slight loss of intensity). |

TABLE 7

| | Fragrance No. 2 + 0.5% of the mixture of the invention | | | |
| --- | --- | --- | --- | --- |
|  | Comparative Test 1 | Test 2 | Test 3 | Test 4 |
|  | Composition of the mixture | | | |
| OCTYL METHOXYCINNAMATE | 82.3 | 70 | 50 | 35 |
| BMDBM | 17.7 | 15 | 35 | 50 |
| BUTYLENE GLYCOL DICAPRYLATE/DICAPRATE | 0 | 15 | 15 | 15 |
| STOVE 45° C. | Compliant | Compliant | Compliant | Compliant |
| STABILITIES 4° C. | Compliant | Compliant | Compliant | Compliant |
| SUN TEST 12 H | Decoloration | Compliant | Compliant | Compliant |
| SENSORY ASSESSMENT | Compliant | Compliant | Compliant | Compliant |
| OLFACTORY AFTER 12 H OF SUN TEST | Loss of intensity of the olfactory note | Compliant | Compliant | Compliant |

TABLE 8

|  |  | Fragrance No. 2 only | Fragrance No. 2 + 0.5% Comparative test 1* | Fragrance No. 2 + 0.5% Mixture 2 | Fragrance No. 2 + 0.5% Mixture 3 | Fragrance No. 2 + 0.5% Mixture 4 |
|---|---|---|---|---|---|---|
| STOVE STABILITIES | 45° C. 4° C. | Compliant White deposit | Compliant Compliant | Compliant Compliant | Compliant Compliant | Compliant Compliant |
| SUN TEST 12 H |  | Complete decoloration | Decoloration | Compliant (slightly decoloured) | Compliant (slightly decoloured) | Compliant (slightly decoloured) |
| SENSORY ASSESSMENT |  | — | Compliant | Compliant (no greasy effect on the skin) | Compliant (no greasy effect on the skin) | Compliant (no greasy effect on the skin) |
| OLFACTORY AFTER 12 H OF SUN TEST |  | Loss of intensity of the olfactory note | Loss of intensity of the olfactory note | Complies with the control | Complies with the control | Complies with the control |

*cf. composition of the mixture "Comparative test 1" in Table 7.

EXAMPLE 2

Lightening Lotion for the Face

A lotion was prepared according to the following formula:

| Perfume concentrate No. 1 from example 1 | 4% |
|---|---|
| Additive according to the invention (Mixture 1 in example 1) | 0.5% |
| PPG-3 Myristyl ether | 5% |
| Glycerin | 2% |
| Carbomer | 0.2% |
| Butylene glycol | 3% |
| Polysorbate 20 | 0.2% |
| Calcium D-pantetheine-S-sulphonate | 0.2% |
| Citrus Extract unshiu | 2% |
| Ethanol | 28% |
| Water | q.s. 100% |
| Neutralizing agent, Preservatives | 0.9% |

This lotion for lightening the complexion is used after make-up removal and cleaning of the skin.

The additive incorporated in the lotion makes it possible to stabilize the solution with respect to the action of UV, in particular by preserving the olfactory identity imparted to the lotion by the perfume concentrate of the formula.

EXAMPLE 3

Hydrating Balsam for the Lips

An anhydrous balsam was prepared according to the following formula, in which the proportions are percentages by weight.

This balsam is transparent and contains a small amount of a perfume concentrate:

| Polymer of the ATPA type * | 16 |
|---|---|
| Ethylhexyl hydroxystearate | 15 |
| Hydrogenated polyisobutene | 46 |
| Cetyl alcohol 95% | 2 |
| Propylene glycol dibenzoate | 20 |
| Additive according to the invention (Mixture 3 in example 1) | 0.4 |
| Perfume Concentrate and Antioxidant | 0.6 |

* The polymer of the ATPA type has the INCI name Bis-Dioctadecylamide Dimer Dilinoleic Acid/Ethylenediamine Copolymer.

The additive according to the invention was added to the formula of the balsam so as to stabilize the organoleptic properties of the transparent composition with respect to the action of UV.

The invention claimed is:

1. An anti-ultraviolet additive comprising at least 95 wt. % of a mixture consisting of
   one or more organic lipophilic $UV_A$ filters,
   one or more organic lipophilic $UV_B$ filters, wherein at least one of the one or more lipophilic $UV_B$ filters is different from at least one of the one or more organic lipophilic $UV_A$ filters, and
   from 1 to 50 wt. % of at least one non-volatile oil that is a solvent for said one or more organic $UV_A$ filters and said one or more organic $UV_B$ filters,
   wherein the amount of the at least one non-volatile oil is sufficient to enhance a UV filtering property of the filters as compared to that of where the at least one non-volatile oil is not present in the additive.

2. The additive according to claim 1, wherein the mixture comprises at most two UV filters.

3. The additive according to claim 1, wherein at least one of the $UV_A$ and $UV_B$ filters is solid at 25° C.

4. The additive according to claim 1, wherein the organic $UV_A$ filter is selected from dibenzoylmethane derivatives and menthyl anthranilate.

5. The additive according to claim 1, wherein the $UV_A$ filter represents from 5 to 75 wt. % of the weight of the additive.

6. The additive according to claim 1, wherein the organic filter filtering $UV_B$ is selected from salicylic derivatives; cinnamate derivatives; derivatives of benzylidene camphor; derivatives of triazine; para-aminobenzoates; derivatives of imidazolines and derivatives of benzal malonate.

7. The additive according to claim 1, wherein the $UV_B$ filter represents from 20 to 90 wt. % of the weight of the additive.

8. The additive according to claim 1, wherein the non-volatile oil represents from 5 to 30 wt. % of the weight of the additive.

9. The additive according to claim 1, wherein the non-volatile oil is selected from aliphatic mono- and diesters, non-hydroxylated aromatic esters, aliphatic carbonates and phenylated silicones.

10. The additive according to claim 1, wherein the non-volatile oil is selected from isononyl isononanoate, butylene glycol dicaprylate/dicaprate, phenyltrimethicone, diisostearyl malate, $C_{12}$-$C_{15}$ alkyl benzoate and dicapryl carbonate.

11. A transparent or translucent composition comprising a perfume or a dye, and an anti-ultraviolet additive consisting of
   an organic $UV_A$ filter,
   an organic $UV_B$ filter that is different from the organic $UV_A$ filter, and from 1 to 50 wt. % of at least one non-volatile oil that is a solvent for said organic $UV_A$ filter and said organic $UV_B$ filter, the organic filters representing from 0.1 to 3.5 wt. % of the weight of the composition wherein the anti-ultraviolet additive is present in an amount sufficient to protect organoleptic properties of the composition against UV radiation, and impede degradation of smell and color of the composition when exposed to UV light.

12. A composition according to claim 11 that is in the form of a serum, a lotion, a cream, a hydrogel, a mask, a stick, a balsam, a patch, a make-up product of the lipstick type, mascara or foundation, or a perfuming solution.

13. A cosmetic composition for care or make-up of the skin comprising the composition according to claim 11.

14. A perfuming solution comprising the composition according to claim 11.

15. The additive according to claim 1, wherein the $UV_A$ filter represents from 10 to 55 wt. % of the weight of the additive.

16. The additive according to claim 1, wherein the $UV_B$ filter represents from 30 to 75 wt. % of the weight of the additive.

17. The additive according to claim 1, wherein the non-volatile oil represents from 10 to 20% of the weight of the additive.

18. The additive according to claim 1, wherein the non-volatile oil represents 15 wt. % of the weight of the additive.

19. The additive according to claim 1, wherein the filters are dissolved in the at least one non-volatile oil.

20. The additive according to claim 11, wherein the transparent or translucent composition is an alcoholic or aqueous-alcoholic solution.

* * * * *